US008818486B2

(12) United States Patent
Montag (10) Patent No.: US 8,818,486 B2
(45) Date of Patent: Aug. 26, 2014

(54) POSITION AND ORIENTATION ALGORITHM FOR A SINGLE AXIS SENSOR (75) Inventor: Avram Dan Montag, Haifa (IL)

(73) Assignee: Biosense Webster (Israel) Ltd., Yokneam (IL)

(*) Notice: Subject to any disclaimer, the term of this patent is extended or adjusted under 35 U.S.C. 154(b) by 16 days.

(21) Appl. No.: 13/547,302

(22) Filed: Jul. 12, 2012

(65) Prior Publication Data
US 2014/0018662 A1    Jan. 16, 2014

(51) Int. Cl.
*A61B 5/05* (2006.01)
*G01B 7/14* (2006.01)
*G06F 7/60* (2006.01)

(52) U.S. Cl.
USPC ........... 600/409; 600/424; 324/207.13; 703/2

(58) Field of Classification Search
USPC ............... 600/409, 424; 703/2; 324/202, 244, 324/245, 247, 248, 307, 207.13
See application file for complete search history.

(56) References Cited

U.S. PATENT DOCUMENTS

| 5,307,072 A | 4/1994 | Jones, Jr. |
| 6,335,617 B1 | 1/2002 | Osadchy et al. |
| 7,277,834 B2 | 10/2007 | Bar Tal et al. |
| 7,912,673 B2 * | 3/2011 | Hebert et al. ................. 702/153 |
| 2007/0167722 A1 | 7/2007 | Bladen et al. |
| 2010/0210939 A1 | 8/2010 | Hartmann et al. |

FOREIGN PATENT DOCUMENTS

| EP | 2186474 B1 | 1/2012 |
| WO | WO 00/27281 A1 | 5/2000 |
| WO | WO 2010/058390 A1 | 5/2010 |

OTHER PUBLICATIONS

European Search Report dated Oct. 11, 2013 for Application No. EP13176185.

* cited by examiner

*Primary Examiner* — Michael Rozanski
(74) *Attorney, Agent, or Firm* — Louis J. Capezzuto (57) ABSTRACT

A method includes generating a magnetic field in a predefined volume. A reference model is defined, which models the magnetic field at multiple points in the volume using spherical harmonics. The magnetic field is measured by a field detector, which is coupled to an intra-body probe inserted into an organ of a living body located in the volume. A cost function is defined by comparing the measured magnetic field with the reference magnetic field model within the volume. The cost function is minimized by a computation over dipole terms in a derivative over the cost function so as to find a position and orientation that matches the measured magnetic field. The found position and orientation is outputted as the position and orientation of the probe in the organ.

20 Claims, 4 Drawing Sheets

POSITION AND ORIENTATION ALGORITHM FOR A SINGLE AXIS SENSOR

FIELD OF THE INVENTION

The present invention relates generally to catheter navigation, and particularly to methods and systems for locating the position and orientation of a catheter.

BACKGROUND OF THE INVENTION

A wide range of medical procedures involve the position and tracking of a catheter within a body. U.S. Patent Application 2007/0167722, which is incorporated herein by reference, describes methods and apparatus for locating the position, preferably in three dimensions, of a sensor by generating magnetic fields which are detected at the sensor. The magnetic fields are generated from a plurality of locations and, in one embodiment of the invention, enable both the orientation and location of a single coil sensor to be determined. The present invention thus finds application in many areas where the use of prior art sensors comprising two or more mutually perpendicular coils is inappropriate.

U.S. Patent Application 2010/0210939, which is incorporated herein by reference, describes a surgical navigation system for tracking an instrument relative to a patient. The system can track a portion of the patient, an instrument, and/or both relative to image data, a coordinate system, an atlas, a morphed atlas, or combinations thereof. The system can include a tracking device on the instrument to provide six degree of freedom information regarding the location of the instrument.

U.S. Pat. No. 7,277,834, which is incorporated herein by reference, describes a method for adapting electromagnetic (EM) field model parameters including the steps of minimizing the difference between a model for the measurements and one or more measurements. The minimization may be done by estimating model parameters, and at least position and/or orientation. The model may further include system model parameters, wherein the system may include one or more sensors and one or more radiators.

U.S. Pat. No. 6,335,617, which is incorporated herein by reference, describes a method for calibrating a magnetic field generator, including fixing one or more magnetic field sensors to a probe in known positions and orientations and selecting one or more known locations in the vicinity of the magnetic field generator. The magnetic field generator is driven so as to generate a magnetic field. The probe is moved in a predetermined, known orientation to each of the one or more locations, and signals are received from the one or more sensors at each of the one or more locations. The signals are processed to measure the amplitude and direction of the magnetic field, at the respective positions of the one or more sensors and to determine calibration factors relating to the amplitude and direction of the magnetic field in the vicinity of the magnetic field generator.

U.S. Pat. No. 5,307,072, which is incorporated herein by reference, describes a method and apparatus for determining the position and orientation of a remote object relative to a reference coordinate frame includes a source having a plurality of field-generating elements for generating electromagnetic fields, a drive for applying, to the generator element, signals that generate a plurality of electromagnetic fields that are distinguishable from one another, a remote sensor having a plurality of field-sensing elements for sensing the fields generated by the source, and a processor for processing the outputs of the sensing elements into remote object position and orientation relative to the source reference coordinate frame. The processor compensates the position and orientation values as a function of displacement of either the field-generating elements from a common center, or the field-sensing elements from a common center, or both. Techniques are disclosed for compensating for small-scale non-concentricity in order to overcome imperfections in the orthogonal coil sets wound on a common core, each set defining the source or the sensor. Techniques are also disclosed for compensating for large-scale non-concentricity to allow physical separation of the coil set defining the source or the sensor to dispersed locations that may be more desirable for a particular application.

SUMMARY OF THE INVENTION

An embodiment of the present invention provides a method including generating a magnetic field in a predefined volume. A reference model is defined, which models the magnetic field at multiple points in the volume using spherical harmonics. The magnetic field is measured by a field detector, which is coupled to an intra-body probe inserted into an organ of a living body located in the volume. A cost function is defined by comparing the measured magnetic field with the reference magnetic field model within the volume. The cost function is minimized by a computation over dipole terms in a derivative over the cost function so as to find a position and orientation that matches the measured magnetic field. The found position and orientation is outputted as the position and orientation of the probe in the organ.

In some embodiments, defining the reference model includes using a magnetic sampling detector scanned within a predefined volume to measure the magnetic field and fitting the magnetic field measurements from the magnetic sampling detector to the reference model. In other embodiments, measuring the magnetic field by the field detector includes measuring a received signal from a single axis sensor near a distal tip of a catheter in the volume. In yet other embodiments, defining the cost function includes utilizing spherical harmonics up to fourth order terms in the reference model.

In some embodiments, minimizing the cost function includes utilizing a Levenberg-Marquardt variation of the Gauss-Newton method. In other embodiments, minimizing the cost function includes constraining an orientation vector to be a unit vector, and choosing the orientation vector from one of six unit vectors in a rigid rotation vector set. In yet other embodiments, minimizing the cost function by the computation over dipole terms in the derivative over the cost function includes replacing higher order terms of derivatives in a Jacobian matrix by the dipole field terms.

In some embodiments, minimizing the cost function by the computation over dipole terms in the derivative over the cost function includes truncating higher order terms of derivatives of spherical harmonics in a Jacobian matrix. In other embodiments, minimizing the cost function includes choosing an initial orientation from among six unit vectors in a rigid rotation vector set, and subsequently varying the position and orientation in an iteration loop.

In some embodiments, outputting the found position and orientation includes calculating respective magnitudes of differential changes in the position and orientation between successive iteration loop cycles, and reporting the position and orientation of the probe upon finding that the magnitudes are less than a predefined threshold.

There is also provided, in accordance with embodiments of the present invention, an apparatus including a field detector and a processor. The field detector is coupled to an intra-body probe inserted into an organ of a living body located in a predefined volume, and configured to measure a magnetic field generated in the volume. The processor is configured to define a reference model, which models the magnetic field at multiple points in the volume using spherical harmonics, and a cost function by comparing the measured magnetic field with the reference magnetic field model within the volume, to minimize the cost function by a computation over dipole terms in a derivative over the cost function so as to find a position and orientation that matches the measured magnetic field, and to output the found position and orientation as the position and orientation of the probe in the organ.

The present invention will be more fully understood from the following detailed description of the embodiments thereof, taken together with the drawings in which:

DETAILED DESCRIPTION OF EMBODIMENTS

Overview

Embodiments of the present invention provide a method for locating an intra-body probe within an organ of a human body. The intra-body probe, typically a catheter, is percutaneously inserted into the body and navigated through the body to the desired organ during a therapeutic medical procedure, such as RF ablation of cardiac tissue. A magnetic field detector, or sensor, at a distal tip of the catheter creates a signal in response to applied magnetic fields from sources near a region in which the body is located. A position and orientation (P&O) algorithm is then implemented to compute a position and an orientation of the sensor within the catheter comprising a single axis sensor by comparing a measured signal in the sensor to a magnetic field reference model. The orientation is the axial vector through the catheter used in calculating the trajectory of the catheter tip while moving through the body that will be described later.

In the embodiments presented here, the reference magnetic field model is first defined using a spherical harmonic representation to describe the magnetic fields in a volume due to one or more magnetic field sources near the volume. Next, a cost function is defined which comprises a difference between the received field at the distal tip of the catheter and the spherical harmonic based magnetic field reference model. The cost function is then minimized using an optimization method for finding the position of the catheter in an organ of the body by choosing an arbitrary initial position vector, but an initial orientation vector discretely from a predefined set of vectors. The position and orientation vectors are then varied continuously in an iteration loop. The optimization method further comprises computing a Jacobian matrix (or derivative) of the cost function over the catheter position and orientation parameters, and approximating the derivative terms in the Jacobian matrix by dipole field terms. This overall P&O tracking method described herein improves computational efficiency and speed in identifying the position and orientation of the catheter, increases a volume over which the magnetic field models are accurate, and eliminates the need for tri-axial orthogonal magnetic sources.

System Description

Figure 1:
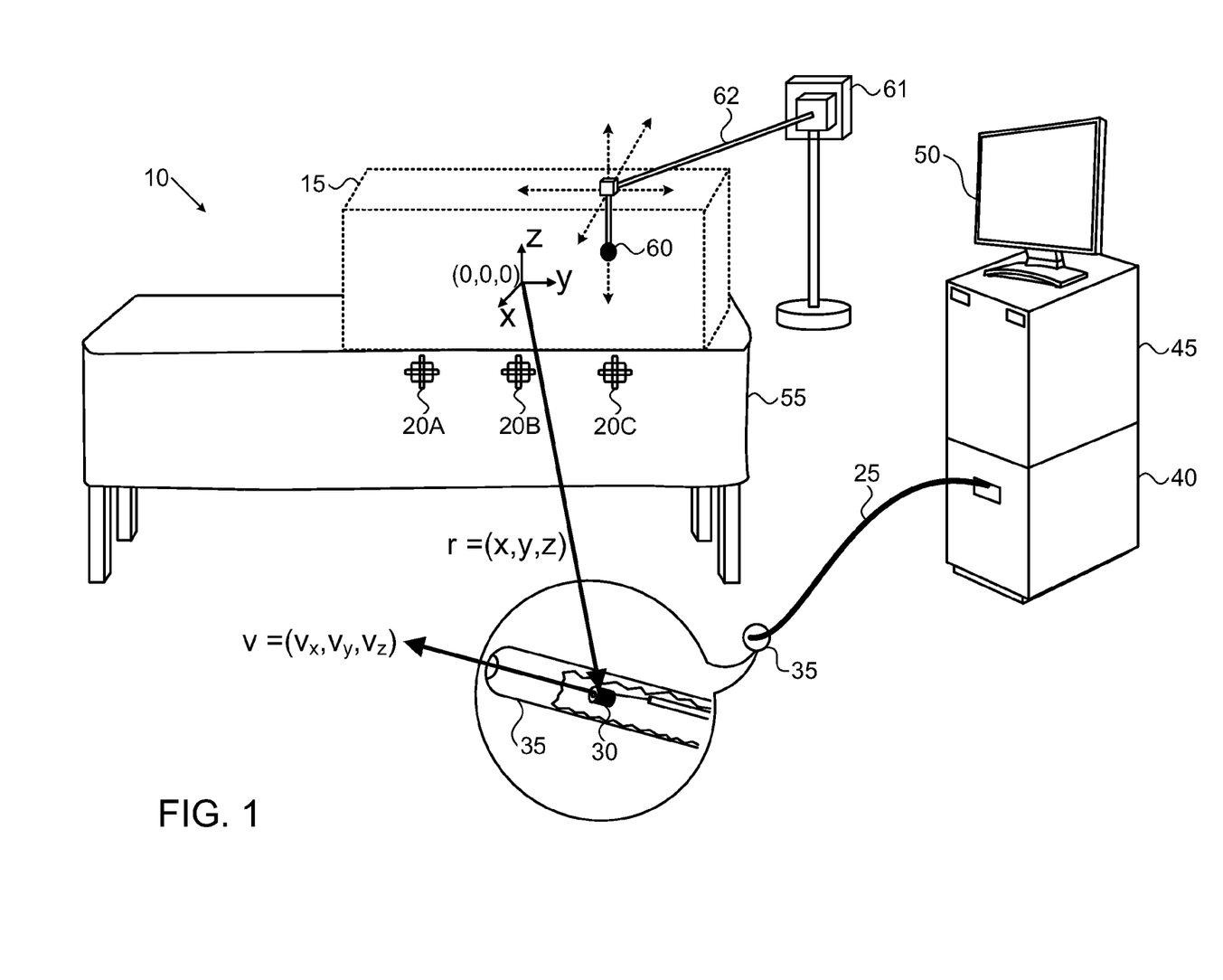
FIG. 1 is a diagram showing a tracking volume for calibrating a magnetic field from magnetic sources in a position and orientation (P&O) tracking system, in accordance with an embodiment of the present invention.

FIG. 1 is a diagram showing a tracking volume 15 for calibrating a magnetic field from magnetic sources in a position and orientation (P&O) tracking system 10, in accordance with an embodiment of the present invention. A magnetic field is generated in a volume 15 due to magnetic field sources 20. Magnetic field sources 20A, 20B, and 20C are also referred to as location pads (LP) or as sources 20.

System 10 identifies the position and orientation of a catheter 25 comprising a detector 30 at a distal tip 35 of the catheter when inserted into an organ of a living body. The catheter is typically used in a therapeutic medical procedure. When catheter 25 is located within the magnetic field generated by sources 20, a signal is magnetically induced in detector 30 at distal tip 35. The induced signal in detector 30 is coupled by the catheter to a receiver 40 in system 10. A processor 45 is configured to identify the position and orientation of catheter tip 35 in response to the signal from receiver 40 in accordance with embodiments described herein.

A display monitor 50 can be used by an operator of system 10. In some embodiments, processor 45 drives display monitor 50 to provide an operator of system 10 with a visual display of the catheter within the organ of the living body. Display monitor 50 may also provide status information and guidance regarding the therapeutic medical procedure that is in progress.

Some elements of processor 45 may be implemented in hardware, e.g., in one or more Application-Specific Integrated Circuits (ASICs) or Field-Programmable Gate Arrays (FPGAs). Additionally or alternatively, some processor elements can be implemented using software, or using a combination of hardware and software elements. In some embodiments, processor 45 comprises a general-purpose computer, which is programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

Catheter detector 30 typically comprises one or more miniaturized coil sensors. In a tri-axial sensor (TAS) used in position and orientation tracking systems, such as the CARTO system (Biosense Webster, Diamond Bar, Calif.), three coils are orthogonally configured at the distal tip of the catheter to create a received signal in response to the magnetic field in order to measure the magnetic field. However, to reduce the area overhead of the distal tip detector, in embodiments of the present invention detector 30 is configured as a single axis sensor (SAS) as shown in FIG. 1 comprising one coil instead of the three coils used in TAS systems. An SAS with one receiving coil does not measure a vector magnetic field as in TAS systems, but only a scalar measurement of the received magnetic field. Detector 30 can also be referred to as SAS 30.

In some embodiments, one or more single axis sensors can be placed near the distal tip of circular loop shaped catheters, such as the LASSO catheter (Biosense Webster, Diamond Bar, Calif.). The diameter of the circular loop can be controlled by system 10. By applying the P&O algorithm described herein to the one or more sensors along the body of the circular loop catheter, the shape of the circular loop can be detected and output to monitor display 50. The operator of system 10 is provided with a visual display of the loop catheter within the organ of the living body.

An organ of a patient lying on a gurney 55 into which the catheter is inserted will be located in volume 15 as described later. System 10 is calibrated and configured to identify the position and orientation of distal tip 35, using the SAS, within volume 15. Magnetic sources 20A, 20B, and 20C can be placed in any convenient configuration near volume 15 to generate a magnetic field within volume 15, and the magnetic sources may be used to define a coordinate system (x,y,z). Typically, sources 20 are attached to gurney 55 and placed below the patient, i.e., below volume 15. A reference origin (0,0,0) of the coordinate system is defined by system 10, typically in the center of volume 15 as shown in FIG. 1, but the reference can be defined at any suitable position.

The coordinate system (x,y,z) is used to define both the magnetic field and the position of the SAS within volume 15. The position and orientation of SAS 30 is defined by an orientation (direction) vector $\vec{v}=(v_x, v_y, v_z)$ located at a position vector $\vec{r}=(x,y,z)$ of the SAS relative to the defined origin as shown in FIG. 1. Although the SAS defined by position $\vec{r}$ and orientation $\vec{v}$ will typically be located in region 15, the SAS is shown under the gurney in FIG. 1 merely for conceptual clarity in defining of the position and orientation vectors. In addition, processor 45 is configured to identify the position and orientation of distal tip 35 of catheter 25, or any other suitable position on the body of catheter 25 from the identified position and orientation vectors of SAS 30 and the known mechanical dimensions of the catheter.

In an embodiment of the present invention, an algorithm for locating the distal tip of the catheter uses a mathematical reference model of magnetic field in tracking volume 15 with the same coordinate system (x,y,z) defined above. Prior to the medical procedure referred to above, a magnetic sampling detector 60 is scanned within volume 15, whose position is defined relative to (0,0,0). In some embodiments, the position of detector 60 is tracked using either a laser or optical tracking system, which is controlled by a robotic system 61, such that detector 60 mounted on a horizontal arm 62 can be scanned anywhere within volume 15. Magnetic field measurements are then made by sampling detector 60 at predefined positions within volume 15 and are used as mathematical boundary conditions for fitting the mathematical reference model to the magnetic field measurements in volume 15 created by magnetic sources 20A, 20B, and 20C.

Since the tracking volume 15 does not comprise any magnetic sources, i.e. sources 20, a magnetic field, formulated from a reference model, and denoted $\vec{B}_{model}$ in the tracking volume can be derived from the Maxwell's equation for no magnetic (current) sources, i.e.

$$\nabla \times \vec{B}_{model} = 0 \quad (1)$$

The magnetic field can be further derived from the magnetic scalar potential $\Phi_M$ in Laplace's equation.

$$\nabla^2 \Phi_M = 0 \quad (2)$$

The magnetic field can be determined from the gradient of the magnetic scalar potential by $$\vec{B}_{model} = -\nabla \Phi_M \quad (3)$$

In embodiments of the present invention, the magnetic scalar potential is modeled here using spherical harmonics, which is of the form $$\Phi_M(r, \theta, \phi) = \sum_{l=0}^{\infty} \sum_{m=-1}^{1} \frac{a_{lm}}{(l2+1)r^{l+1}} Y_{lm}(\theta m) \quad (4)$$

where $Y_{lm}(\theta,\phi)$ are the spherical harmonics, $a_{lm}$ are real coefficients, and a spherical coordinate system $(r,\theta,\phi)$ is defined using the same origin (0,0,0) which is coincident with the Cartesian coordinate system defined above.

The magnetic field distribution in tracking volume 15 can be determined by inserting the magnetic scalar potential of equation (4) into equation (3). Real coefficients $a_{lm}$ are derived from a set of magnetic measurements obtained from magnetic sampling detector 60 as described above.

Although the magnetic field model in tracking volume 15 is defined initially using spherical coordinates, the P&O algorithm described later uses Cartesian coordinates. Coordinate transformations known in the art are used to transform the spherical coordinates $(r,\theta,\phi)$ to Cartesian coordinates (x,y,z), and vice versa.

In some embodiments, the magnetic field reference model $\vec{B}_{model}(x,y,z)$ in volume 15 may comprise a fitted magnetic field due to an individual magnetic source. In other embodiments, $\vec{B}_{model}$ may comprise all of the magnetic sources operating simultaneously, or any combination of the one or more magnetic sources (e.g., location pads 20A, 20B, 20C) sequentially operating thereof. In other embodiments, the magnetic field reference model may also comprise parameters related to operating the one or more magnetic sources at different frequencies. Yet in other embodiments, the model may also comprise the field due to operating one or more of the three individual coils sequentially within a tri-axial coil source. In another embodiment, the model may comprise the field due to one or more single coil sources at different positions near volume 15.

In embodiments of the present invention, since the reference model as described previously is derived by fitting magnetic measurements as boundary conditions, no information is required about the shape, structure, or positions of the magnetic sources, e.g. the location pads. Thus, such embodiments preclude the need for well-defined tri-axial magnetic coil-based sources. Well-defined sources are required for the triangulation techniques used for catheter tracking, for example, in the CARTO system as referenced previously. Moreover, the inventors have found that the accuracy of the reference model defined using the approach described herein is not limited to the distal tip of the catheter being only within the pre-calibrated tracking volume. P&O tracking accuracy is still maintained when the distal tip of the catheter exceeds the boundary size of tracking volume 15 by 150 mm in both the X and Y directions, and better than prior art tracking systems.

Figure 2:
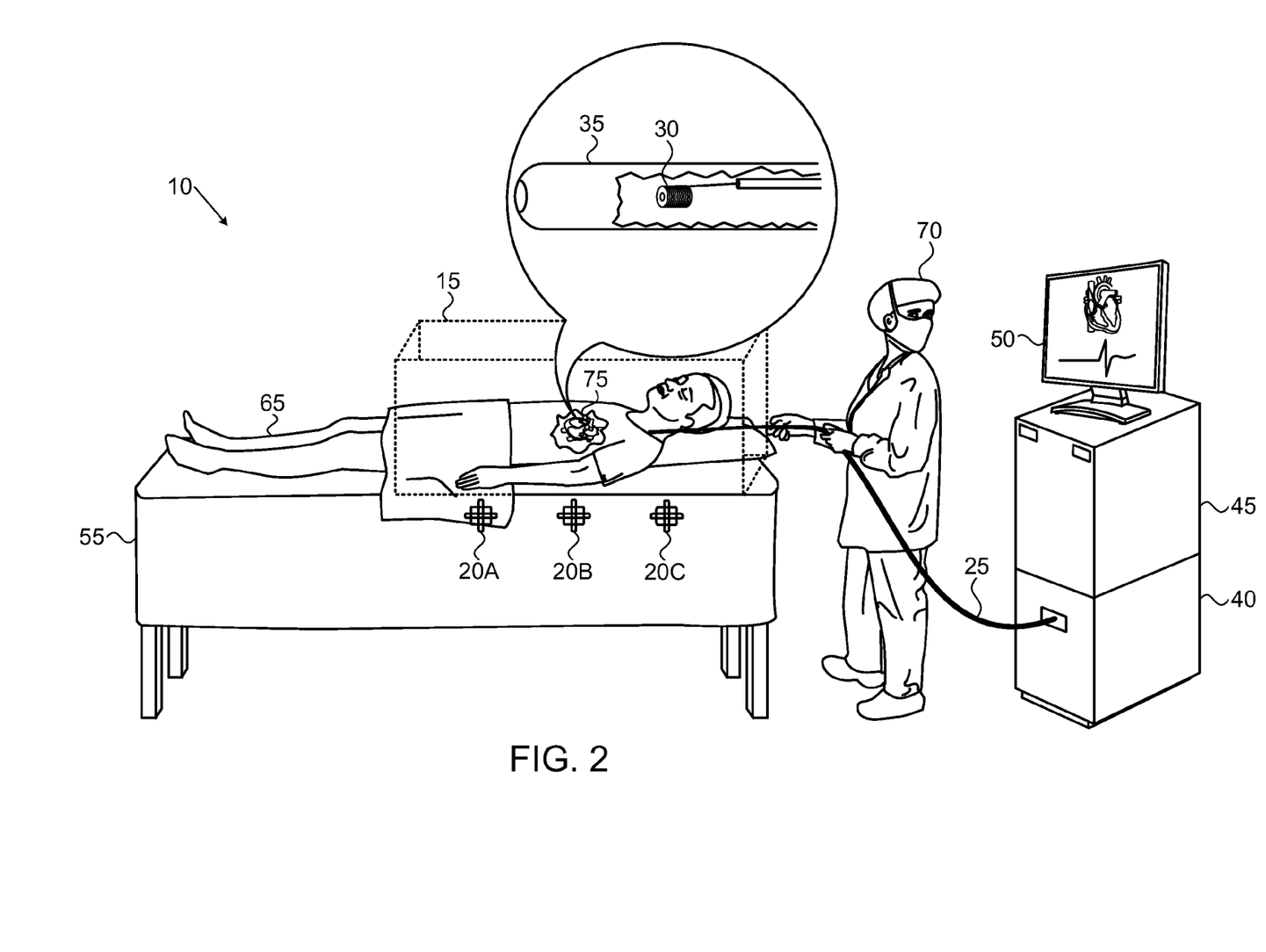
FIG. 2 is a diagram showing a position and orientation (P&O) tracking system, in accordance with an embodiment of the present invention.

FIG. 2 is a diagram showing a position and orientation (P&O) tracking system, in accordance with an embodiment of the present invention. System 10 in FIG. 2 shows a living body 65 (e.g., a patient) laying on gurney 55. An operator 70 percutaneously inserts catheter 25 comprising SAS 30 at distal tip 35 into an organ 75, typically a heart, which is located within magnetic field calibrated volume 15.

In embodiments of the present invention, a received signal detected by SAS 30 (in response to the magnetic field in volume 15 created by location pads 20A, 20B and 20C) is coupled to receiver 40 in system 10. Processor 45 is configured to identify the position and orientation of catheter tip 35 by use of the P&O algorithm. The algorithm is a function of both the measured signal from SAS 30 and the mathematical model of the magnetic field in volume 15 as described previously.

An estimated measurement Mest at the SAS is given by the dot product of the orientation vector of the SAS with the magnetic field $\vec{B}_{model}(x,y,z)$, i.e.

$$Mest = \vec{v} \cdot \vec{B}_{model} \quad (5)$$

Unlike the TAS which maps the orientation vector into a vector projection of the local magnetic field and provides receiver 40 with a vector representation of the received field, the SAS provides only a scalar measurement of the projection of the received magnetic field in the direction of the sensor axis given by Equation (5). For example, consider the case of a magnetic field generated by three tri-axial magnetic sources where each of the three orthogonal coils are operated separately and detected by an SAS at the catheter distal tip. Such a system would yield nine Mest values where the $i^{th}$ value is denoted $Mest_i$.

In some embodiments, a difference function is defined by $$\Delta Meas_i = Mest_i - meas_i \quad (6)$$

where $meas_i$ is the actual measured field in the SAS. A cost function cost is defined by the sum of the squares of the difference function in Equation (6).

$$cost = \sum_{i=1}^{10} \Delta Meas_i^2 \quad (7)$$

where $\Delta Meas_{10}$ is a penalty function given by $$\Delta Meas_{10} = constraintWeight(v_x^2 + v_y^2 + v_z^2 - 1) \quad (8)$$

and constraintWeight is a constant typically with a value of constraintWeight=0.5. The cost function cost from equation (7) is the summation over the nine values of $\Delta Meas_i^2$ for the case of three tri-axial magnetic sources and the penalty function term of Equation (8).

In embodiments of the present invention, the P&O algorithm is based on an optimization method which minimizes the cost function, cost, given by Equation (7). The cost function is dependent on the SAS orientation vector $\vec{v} = (v_x, v_y, v_z)$ and SAS position vector $\vec{r} = (x,y,z)$. The minimization of the cost function occurs in an iteration loop which changes the values of the SAS orientation vector and the SAS position vector.

In some embodiments, a Levenberg-Marquardt (L-M) variation of the Gauss-Newton (G-N) optimization method is used to minimize the cost function based on a sum of square terms as shown in Equations (6) and (7). This method comprises computing the Jacobian matrix J with derivatives of the cost function with respect to the six variables x, y, z, $v_x$, $v_y$, and $v_z$. The L-M variation of the G-N method comprises a computation of six differential variables ($\partial x$, $\partial y$, $\partial z$, $\partial v_x$, $\partial v_y$, $\partial v_z$) in the iteration loop as given by $$\begin{pmatrix} \partial x \\ \partial y \\ \partial z \\ \partial v_x \\ \partial v_y \\ \partial v_z \end{pmatrix} = -(J^T J + \lambda \operatorname{diag}(J))^{-1} J^T \Delta Meas \quad (9)$$

where $J^T$ is the transpose of J, diag(J) is a diagonal matrix whose elements are the diagonal elements of J, and $\lambda$ is a non-negative scalar parameter used in the P&O algorithm. In computing the Jacobian J, the spatial derivatives of $\Delta Meas_i$ from Equation (6), which are essentially the derivatives of $Mest_i$, comprise the product of the orientation vector $\vec{v}$ with the spatial derivatives of $\vec{B}_{model}$. $\Delta Meas$ in equation (9) is a 10×1 matrix, which comprises nine terms from the tri-axial sources and one penalty function term from equation (8).

The six differentials ($\partial x$, $\partial y$, $\partial z$, $\partial v_x$, $\partial v_y$, $\partial v_z$) computed iteratively from equation (9) represent the differential changes of the components of position vector $\vec{r} = (x,y,z)$, and the differential changes of the components of orientation vector $\vec{v} = (v_x, v_y, v_z)$ between successive iteration loop cycles in the P&O algorithm. In some embodiments, the iteration loop is terminated when the respective magnitudes of the change in the position vector $|\partial \vec{r}| = \sqrt{(\partial x)^2 + (\partial y)^2 + (\partial z)^2}$ and the change in the orientation vector $|\partial \vec{v}| = \sqrt{(\partial v_x)^2 + (\partial v_y)^2 + (\partial v_z)^2}$ between iteration loop cycles are below a predefined threshold, typically $|\partial \vec{r}| < 0.002$ and $|\partial \vec{v}| < 0.002$.

During the iteration loop of the P&O algorithm, the cost function typically decreases monotonically as the position and orientation parameters are varied in the loop. When the threshold levels $|\partial \vec{r}| < 0.002$ and $|\partial \vec{v}| < 0.002$ are reached, the position and orientation vectors yielding these threshold values from equation (9) are assigned by system 10 to be the actual position and orientation vectors. The P&O algorithm described herein has empirically exhibited orientation and position accuracies to within 1 mm.

In some embodiments of the present invention, the inventor has found empirically that a number of approximations made to the P&O algorithm in minimizing the cost function ensure convergence stability and computational efficiency in the iteration loop. First, the orientation vector $\vec{v} = (v_x, v_y, v_z)$ is constrained in the algorithm to be a unit vector, namely, $$v_x^2 + v_y^2 + v_z^2 = 1 \quad (10)$$

Secondly, the algorithm is constrained to use spherical harmonics only up to the $4^{th}$ Order. Finally, the derivatives of the cost function, comprising higher order spherical harmonic terms used in the Jacobian matrix J, are replaced with dipole field terms as will be described below.

In some embodiments, a dipole magnetic field model $\vec{B}_{dipole}$, which is also fit to the magnetic field data in volume 15 from magnetic sampling detector 60 in volume 15, is also derived in parallel to the spherical harmonic based model $\vec{B}_{model}$ described previously. The field components of $\vec{B}_{dipole}$ due to three tri-axial dipole transmitters are given in the matrix below as $$\begin{pmatrix} \dfrac{-2x^2+y^2+z^2}{(x^2+y^2+z^2)^{5/2}} & -\dfrac{3xy}{(x^2+y^2+z^2)^{5/2}} & -\dfrac{3xz}{(x^2+y^2+z^2)^{5/2}} \\ -\dfrac{3xy}{(x^2+y^2+z^2)^{5/2}} & \dfrac{x^2-2y^2+z^2}{(x^2+y^2+z^2)^{5/2}} & -\dfrac{3yz}{(x^2+y^2+z^2)^{5/2}} \\ -\dfrac{3xz}{(x^2+y^2+z^2)^{5/2}} & -\dfrac{3yz}{(x^2+y^2+z^2)^{5/2}} & \dfrac{x^2+y^2-2z^2}{(x^2+y^2+z^2)^{5/2}} \end{pmatrix} \quad (11)$$

Spatial derivatives of $\vec{B}_{dipole}$ create terms that are proportional to $(x^2+y^2+z^2)^{-5/2}$ and $(x^2+y^2+z^2)^{-7/2}$ whereas the spatial derivatives of $\vec{B}_{model}$ based on spherical harmonics with terms up to the $4^{th}$ order create higher order terms proportional to $(x^2+y^2+z^2)^{-11/2}$ and $(x^2+y^2+z^2)^{-13/2}$.

In some embodiments, it is been determined by the inventor empirically that replacing the spatial derivatives of $\vec{B}_{model}$ based on spherical harmonics with terms up to the $4^{th}$ order with the derivatives of the dipole terms (i.e., terms up to $(x^2+y^2+z^2)^{-7/2}$ shown in equation (11) in the computation of the Jacobian matrix J for the P&O algorithm of equation (9) does not result in any change in accuracy. However, the computational speed and efficiency of the P&O algorithm in system 10 are significantly increased.

In other embodiments, the full spatial derivatives of $\vec{B}_{model}$ based on spherical harmonics up to $4^{th}$ order are computed, but the higher order terms of $(x^2+y^2+z^2)^{-11/2}$ and $(x^2+y^2+z^2)^{-13/2}$ in the derivatives are truncated in the Jacobian used in the P&O algorithm. Here, the inventor also determined empirically that accuracy is still maintained, while the computational speed and efficiency are also increased significantly, relative to using the entire spherical harmonic expansion. However, in the embodiment described here, generating a calibrated $\vec{B}_{dipole}$ model in parallel to $\vec{B}_{model}$ is not needed.

Figure 3:
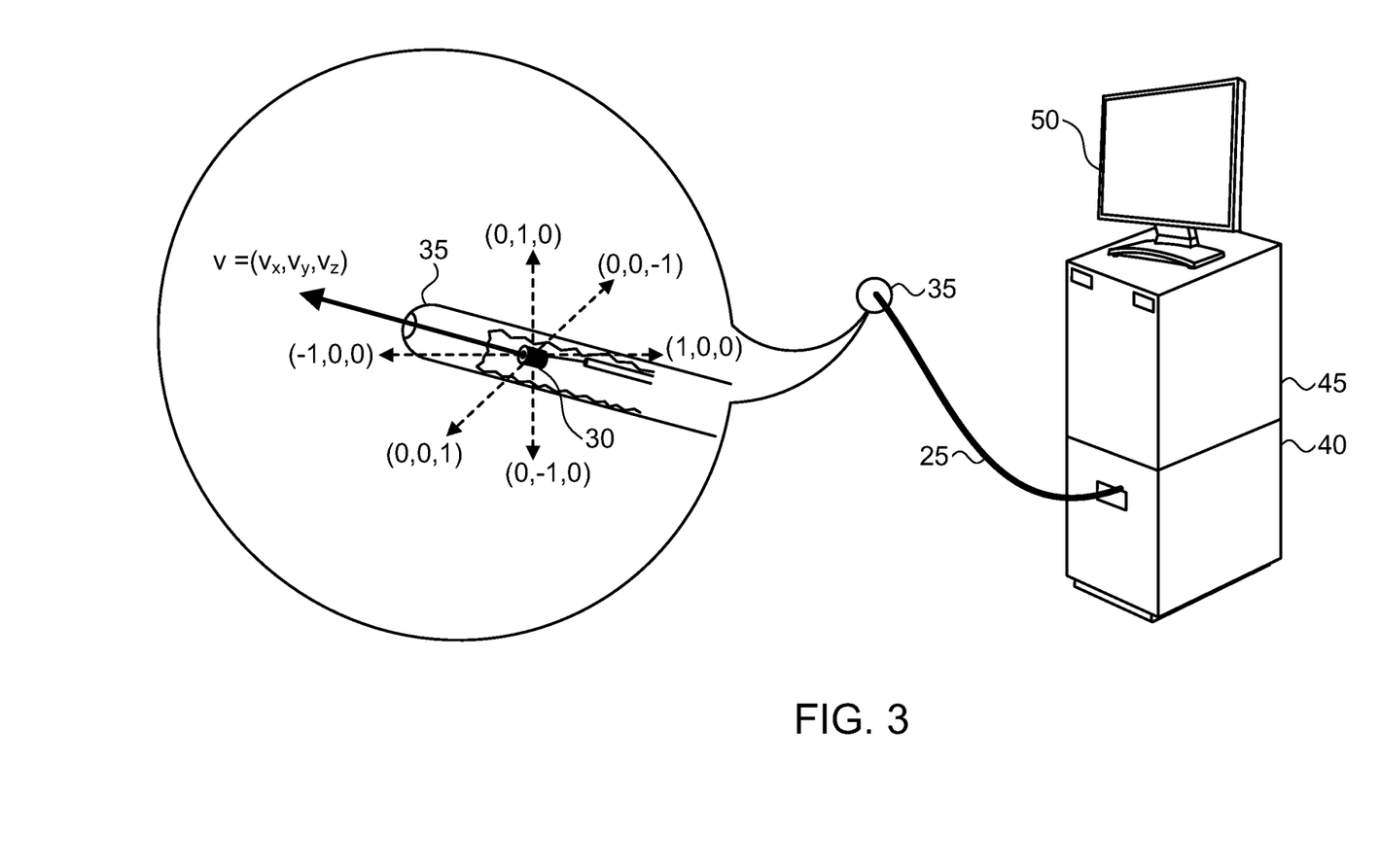
FIG. 3 is a diagram showing a set of six predefined orientation vectors at a distal tip of an intra-body probe utilized in a position and orientation (P&O) tracking system, in accordance with an embodiment of the present invention.

FIG. 3 is a diagram showing a set of six predefined orientation vectors at a distal tip of an intra-body probe utilized in a position and orientation (P&O) tracking system, in accordance with an embodiment of the present invention. When the catheter is first inserted into patient 65, system 10 initially computes the cost function from the position and orientation vectors and the measured field at SAS 30 without any previous information of position and orientation of SAS 30 in accordance with the L-M algorithm described previously.

It has been determined by the inventor empirically that the P&O algorithm described herein may not converge unless the initial orientation vector used in the algorithm is chosen from the unit vector set given by ((1,0,0), (−1,0,0), (0,1,0), (0,−1,0), (0,0,1), (0,0,−1)) as shown in the inset diagram of FIG. 3. An arbitrary position vector is chosen (typically in the center of volume 15) and six cost functions are computed based on the six unit vectors. The orientation vector resulting in the lowest cost function for the six computed cost functions from this vector set is chosen as the initial orientation vector.

Figure 4:
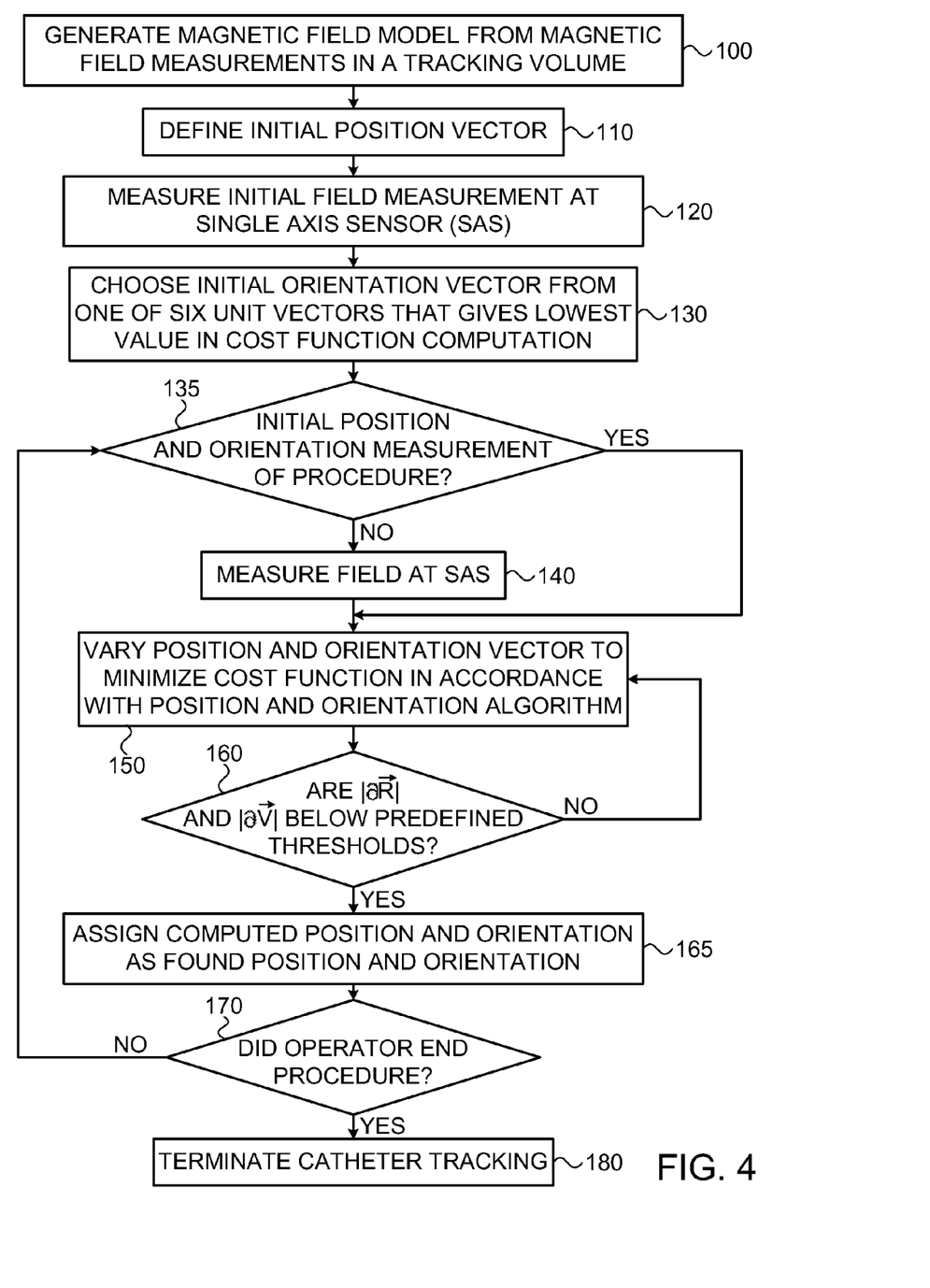
FIG. 4 is a flow chart that schematically illustrates a method for tracking a single axis sensor, in accordance with an embodiment of the present invention.

FIG. 4 is a flow chart that schematically illustrates a method for tracking a single axis sensor, in accordance with an embodiment of the present invention. The flow chart corresponds to steps of the P&O algorithm. In a generation step 100, a magnetic field model $\vec{B}_{model}$ is generated from magnetic field measurements in a tracking volume by a magnetic sampling detector 60 scanned within volume 15 at predefined points. The magnetic field model is fit to the magnetic field measurements at predefined points made by detector 60 in volume 15, as described previously.

At a definition step 110, an initial position vector is defined. The algorithm arbitrarily assigns an initial SAS position vector $\vec{r}=(x,y,z)$ of the distal tip of the catheter, at a point such as the center of tracking volume 15. In a first measurement step 120, initial field measurements of meas$_i$ are measured at single axis sensor 30 (SAS). The field measurements are received by receiver 40 and relayed to processor 45.

In a choosing step 130, an initial orientation vector is chosen from one of six unit vectors, e.g., ((1,0,0), (−1,0,0), (0,1,0), (0,−1,0), (0,0,1), (0,0,1)). Processor 45 computes six cost functions based on equations (6)-(8) using the initial field measurement from step 120, the six unit vectors, and the initial position vector defined in step 110. The initial orientation vector chosen is the one that gives the lowest value of cost in six cost function computations, using equation (7).

In a first decision step 135, if system 10 is measuring the initial position and orientation of the procedure, system 10 bypasses a second measurement step 140, since the fields were already measured in step 120. If not, fields meas$_i$ are measured at single axis sensor 30 (SAS) in second measurement step 140. The field measurement is received by receiver 40 and relayed to processor 45. The fields measured in second measurement step 140 are used to compute the cost function based on equations (6)-(8) for identifying the position and orientation of catheter distal tip 35 moving through organ 75 in all subsequent steps of the algorithm shown in the flow chart of FIG. 4.

In accordance with embodiments of the present invention, processor 45 initiates an iteration loop after step 140 to minimize the cost function value cost in order to identify the position and orientation of the catheter in an organ of a living body. In a varying step 150, the position and orientation vectors are varied to reduce the cost function. The computation also uses equations (1)-(5) to derive values of Mest$_i$.

In accordance with embodiments of the present invention, while in the iteration loop, not only is the cost function being reduced, typically monotonically, but processor 45 also computes the six differential variables $(\partial x, \partial y, \partial z, \partial v_x, \partial v_y, \partial v_z)$ from equation (9). In a second decision step 160, when $|\partial \vec{r}|$ and $|\partial \vec{v}|$ are not below a predefined threshold, typically 0.002 as previously described, the iteration loop continues with varying step 150. If $|\partial \vec{r}|$ and $|\partial \vec{v}|$ are below the predefined threshold, processor 45 assigns the computed position and orientation as the found position and orientation in an assignment step 165, i.e. the measured position and orientation vector of SAS 30. System 10 then assesses if operator 70 ended the procedure in a third decision step 170. The operator can end the procedure, for example, by disconnecting catheter 25 from system 10, or by instructing system 10 accordingly to end the procedure.

In embodiments of the present invention, the P&O algorithm detects the position of distal tip 35 of catheter 25 in a given instant as operator 70 moves catheter 25 through the body of patient 65, and continues tracking the motion of distal tip 35 until operator 70 ends the procedure. In decision step 170, if the operator did not end the procedure, the visual display of the catheter within organ 75 is updated on display monitor 50. System 10 assesses that the initial position and orientation of the procedure is not being measured at step 135, and a new measurement of the field at SAS 30 is measured in step 140 as the P&O tracking procedure continues.

If the operator ends the procedure as detected by system 10, the visual display of the catheter within organ 75 is updated on display monitor 50, and catheter tracking is terminated in a termination step 180. In some embodiments, display monitor 50 may also provide status information and guidance to operator 70 regarding the therapeutic medical procedure.

In the embodiments described above, the position and orientation from a previous P&O iteration loop computation are passed into the next P&O iteration loop computation as shown in FIG. 4. The sampling time between successive P&O measurements as the catheter moves within the patient, i.e., from step 140 to step 170, is typically 16 msec.

In other embodiments, the position vector from the previous P&O iteration loop computation is passed into the next P&O iteration loop computation if the operator did not end the procedure in step 170. However alternatively, the orientation vector for the next P&O iteration loop may be first chosen from the six unit vectors as described previously before entering the P&O iteration loop.

Although the embodiments described herein mainly address tracking the position of a catheter in a heart, the methods and systems described herein can also be used in other applications which track an intra-body probe inserted into an organ of a living body, such as in image guided surgery and radiation therapy. The embodiments described herein can also be utilized in any non-medical application requiring electromagnetic tracking.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method for locating an intra-body probe during a procedure within an organ of a living body, the method comprising:

generating a magnetic field in a predefined volume;

providing an intra-body probe configured to be inserted within an organ of a living body within the predefined volume, the intra-body probe comprising a field detector near a distal tip of the intra-body probe;

defining an initial position vector of the distal tip of the intra-body probe within the organ of the living body;

defining a reference model, which models the magnetic field at multiple points in the volume using spherical harmonics;

measuring the magnetic field with the field detector of the intra-body probe within the organ of the living body located in the volume;

defining a cost function by comparing the measured magnetic field with the reference magnetic field model within the volume;

minimizing the cost function by a computation over dipole terms in a derivative over the cost function so as to find a position and orientation that matches the measured magnetic field;

determining whether differential changes of components of a position vector of the measured magnetic field and differential changes of components of an orientation vector of the measured magnetic field are below predefined thresholds;

outputting the found position and orientation as the position and orientation of the probe in the organ; and terminating tracking of the intra-body probe within the organ of the living body at termination of the procedure.

2. The method according to claim 1, wherein defining the reference model comprises using a magnetic sampling detector scanned within a predefined volume to measure the magnetic field and fitting the magnetic field measurements from the magnetic sampling detector to the reference model.

3. The method according to claim 1, wherein measuring the magnetic field by the field detector comprises measuring a received signal from a single axis sensor near a distal tip of a catheter in the volume.

4. The method according to claim 1, wherein defining the cost function comprises utilizing spherical harmonics up to fourth order terms in the reference model.

5. The method according to claim 1, wherein minimizing the cost function comprises utilizing a Levenberg-Marquardt variation of the Gauss-Newton method.

6. The method according to claim 1, wherein minimizing the cost function comprises constraining an orientation vector to be a unit vector, and choosing the orientation vector from one of six unit vectors in a rigid rotation vector set.

7. The method according to claim 1, wherein minimizing the cost function by the computation over dipole terms in the derivative over the cost function comprises replacing higher order terms of derivatives in a Jacobian matrix by the dipole terms.

8. The method according to claim 1, wherein minimizing the cost function by the computation over dipole terms in the derivative over the cost function comprises truncating higher order terms of derivatives of spherical harmonics in a Jacobian matrix.

9. The method according to claim 1, wherein minimizing the cost function comprises choosing an initial orientation from among six unit vectors in a rigid rotation vector set, and subsequently varying the position and orientation in an iteration loop.

10. The method according to claim 1, wherein outputting the found position and orientation comprises calculating respective magnitudes of differential changes in the position and orientation between successive iteration loop cycles, and reporting the position and orientation of the probe upon finding that the magnitudes are less than a predefined threshold.

11. An apparatus for use during a procedure within an organ of a living body, the apparatus comprising:

a field detector, which is coupled to an intra-body probe near a distal tip of the probe, wherein the probe is configured to be inserted into an organ of a living body located in a predefined volume, and configured to measure a magnetic field generated in the volume; and a processor, which is configured to define an initial position vector of the distal tip of the intra-body probe within the organ of the living body and configured to define a reference model, which models the magnetic field at multiple points in the volume using spherical harmonics, and a cost function by comparing the measured magnetic field with the reference magnetic field model within the volume, to minimize the cost function by a computation over dipole terms in a derivative over the cost function so as to find a position and orientation that matches the measured magnetic field, and to determine whether differential changes of components of a position vector of the measured magnetic field and differential changes of components of an orientation vector of the measured magnetic field are below predefined thresholds and to output the found position and orientation as the position and orientation of the probe in the organ, and to terminate tracking of the intra-body probe within the organ of the living body at termination of the procedure.

12. The apparatus according to claim 11, wherein the processor is configured to define the reference model by using a magnetic sampling detector scanned within a predefined volume to measure the magnetic field and fitting the magnetic field measurements from the magnetic sampling detector to the reference model.

13. The apparatus according to claim 11, wherein the field detector comprises a single axis sensor near a distal tip of a catheter in the volume which is configured to receive a signal in response to the magnetic field in the volume.

14. The apparatus according to claim 11, wherein the processor is configured to define the cost function by utilizing spherical harmonics up to fourth order terms in the reference model.

15. The apparatus according to claim 11, wherein the processor is configured to minimize the cost function by utilizing a Levenberg-Marquardt variation of the Gauss-Newton method.

16. The apparatus according to claim 11, wherein the processor is configured to minimize the cost function by constraining an orientation vector to be a unit vector, and by choosing the orientation vector from one of six unit vectors in a rigid rotation vector set.

17. The apparatus according to claim 11, wherein the processor is configured to minimize the cost function by the computation over dipole terms in the derivative over the cost function by replacing higher order terms of derivatives in a Jacobian matrix by the dipole terms.

18. The apparatus according to claim 11, wherein the processor is configured to minimize the cost function by the computation over dipole terms in the derivative over the cost function by truncating higher order terms of derivatives of spherical harmonics in a Jacobian matrix.

19. The apparatus according to claim 11, wherein the processor is configured to minimize the cost function by choosing an initial orientation from among six unit vectors in a rigid rotation vector set, and by subsequently varying the position and orientation in an iteration loop.

20. The apparatus according to claim 11, wherein the processor is configured to output the found position and orientation by calculating respective magnitudes of differential changes in the position and orientation between successive iteration loop cycles, and by reporting the position and orientation of the probe upon finding that the magnitudes are less than a predefined threshold.

* * * * *